United States Patent [19]

Watts et al.

[11] 4,335,139

[45] Jun. 15, 1982

[54] PHARMACEUTICAL FORMULATIONS CONTAINING PROSTACYCLIN COMPOUNDS

[75] Inventors: Ian S. Watts, Sidcup; Peter H. Marsden, Dartford, both of England

[73] Assignee: Burroughs Wellcome Co., Research Triangle Park, N.C.

[21] Appl. No.: 182,054

[22] Filed: Aug. 28, 1980

Related U.S. Application Data

[63] Continuation of Ser. No. 39,645, May 16, 1979, abandoned.

[30] Foreign Application Priority Data

May 17, 1978 [GB] United Kingdom ............... 20175/78

[51] Int. Cl.$^3$ ............................................. A61K 31/34
[52] U.S. Cl. .................................................. 424/285
[58] Field of Search ........................ 424/305, 317, 285

[56] References Cited

U.S. PATENT DOCUMENTS 4,058,623  11/1977  Rolf-Rudiger .

FOREIGN PATENT DOCUMENTS

| | | |
|---|---|---|
| 2654149 | 6/1977 | Fed. Rep. of Germany . |
| 2720999 | 11/1977 | Fed. Rep. of Germany . |
| 2351112 | 4/1977 | France . |
| 1489780 | 10/1977 | United Kingdom . |
| 1503447 | 3/1978 | United Kingdom . |
| 1504070 | 3/1978 | United Kingdom . |
| 1504437 | 3/1978 | United Kingdom . |

OTHER PUBLICATIONS

Hayashi et al.—Chem. Abst., vol. 90 (1979), pp. 127, 526.
Shirley—Organic Chemistry (1964, Holt), pp. 535–536.
Finar—Organic Chemistry—3rd Edit. (Longmans, 1959), pp. 305–307.

*Primary Examiner*—Sam Rosen
*Attorney, Agent, or Firm*—Donald Brown

[57] ABSTRACT

Stabilized pharmaceutical formulations of prostacyclin or certain analogues thereof comprising an amino acid buffer, optionally containing a base, and the preparation of such formulations.

34 Claims, No Drawings

PHARMACEUTICAL FORMULATIONS CONTAINING PROSTACYCLIN COMPOUNDS

This is a continuation of application Ser. No. 039,645, filed May 16, 1979, now abandoned.

The present invention relates to pharmaceutical compositions containing prostacyclin (PGI$_2$, PGX), 15-methylprostacyclin, 16,16-dimethylprostacyclin, or their pharmaceutically acceptable salts.

Prostacyclin and its salts are important in human medicine and veterinary practice as they have a powerful anti-aggregating action on blood platelets and also accelerate wound healing and prevent, or have a therapeutic effect on, stomach ulcers.

The anti-aggregatory effect on blood platelets is useful, for example, in preventing or mitigating the formation of thrombi or emboli during extracorporeal circulation of blood, e.g. in renal dialysis and cardio-pulmonary by-pass.

However, a difficulty experienced with prostacyclin and its salts is that prostacyclin and its salts are unstable, especially in aqueous solution, and are quickly transformed into 6-oxo-PGF$_{1\alpha}$ and its salts, which are almost pharmacologically inactive and have very few, if any, of the beneficial activities of prostacyclin and its salts.

Prostacyclin and its salts are known to be more stable in alkaline media than in acidic or neutral media. Although some improvement in stability has been obtained by using tris buffer in alkaline solution, the prostacyclin has still been rapidly decomposed. This has meant that the prostacyclin has had to be made up very shortly before use by, say, intravenous infusion, and the pharmacological activity of the solution has changed considerably while it has been waiting to be used. This has made it difficult for the infusion to be controlled as carefully as desirable.

We have now surprisingly found that a marked improvement in stability can be obtained by having the prostacyclin, 15-methylprostacyclin, 16,16-dimethylprostacyclin, or a salt thereof, preferably the sodium salt, (hereinafter referred to as the "active compound"), in association with a pharmaceutically acceptable buffer having a pH value of at least 9 and based on an amino acid as the principal buffering acid in the buffer. The active compound and the buffer may be in association in the solid state and in solution in a solvent, usually water. When the active compound and buffer are in solution, the pH measured is that of the solution containing said active compound and buffer, and said formulation or buffer preferably has a pH of at least 9.

If the active compound and the buffer are in association in the solid state, by pH value of the buffer or the formulation we mean the pH measured in any one of the following ways. If the solid is a frozen solution, then the pH measured is that of the solution resulting from thawing the frozen solution. For other solid states, the pH measured is that of the solution resulting from dissolving the associated active compound and buffer in Water for Injections having a pH value of 7. For the particular case of a freeze dried residue of such a solution, the pH measured is that of the solution resulting from dissolving a sample of the residue in the minimum volume of Water for Injections having a pH value of 7 required to produce a clear solution.

In the solid state, the freeze drying of such a solution results in improved stability of the active compound. Freeze drying may be effected in the conventional manner in, for example, an ampoule or vial. The solution may also be frozen and stored at, say, −20° C. for use as a frozen injection or for diluting on thawing.

Such a solution and all solutions hereinafter referred to are, for medicinal purposes, to be understood to be sterile solutions.

Prostacyclin and analogues thereof, in particular 15-methylprostacyclin and 16,16-dimethylprostacyclin, and a salt of one of these may be prepared by methods described in our co-pending UK Patent Application No. 19384/76 for the preparation of compounds of analogous structure. These include dehydrohalogenation of a compound of formula (I):

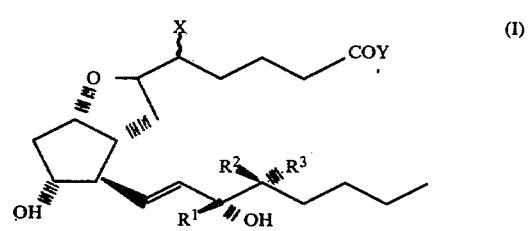

wherein X is bromo or iodo; Y is OH, NHR$^4$ or OR, R being alkyl of 1 to 4 carbon atoms or a pharmaceutically acceptable cation such as sodium, R$^4$ being alkyl of 1 to 4 carbon atoms; R$^1$, R$^2$ and R$^3$ are independently selected from hydrogen and alkyl of 1 to 4 carbon atoms particularly methyl, with a base; for example, when R$^1$ is hydrogen R$^2$ and R$^3$ are both methyl and vice-versa; and converting, if necessary, the resulting compound in which Y is NHR$^4$ or OR, R and R$^4$ being alkyl of 1 to 4 carbon atoms, into the desired active compound.

The amino-acid for use in the buffer is preferably sulphur-free and the most preferred amino-acid is glycine, especially as it is readily available and, if prepared synthetically, does not need to be optically resolved; but other amino-acids such as valine, alanine and arginine may also be used.

The total concentration of amino-acid (i.e. including its salts) in the buffer is preferably as low as is consistent with obtaining a stable buffer, e.g. in the range of from 0.02 M to 0.03 M, preferably about 0.025 M, as the presence of too much amino-acid tends to reduce the stability of the active compound by increasing the ionic strength of a solution of the associated active compound and buffer. The amino-acid must be sufficiently soluble to provide the necessary buffering capacity.

If sodium chloride is present in a solution of the buffer, as is preferred, the amount added should not be such that the solution is pharmaceutically unacceptable. The molar concentration of sodium chloride is preferably about the same as that of the amino-acid. Too much sodium chloride would raise the ionic strength of a solution of the associated active compound and buffer undesirably and adversely affect the stability of the active compound. Other salts, e.g. potassium chloride, may also be present if they, or their amounts, are pharmaceutically acceptable.

The pH of the buffer is preferably 10.2 to 11.6, especially about 10.5, when measured by the appropriate method as hereinabove described.

As an example of preparing a buffer solution according to the invention containing prostacyclin, a solution of glycine in water and also containing some sodium chloride was prepared. To this solution was added sodium hydroxide as base to raise the pH to the desired level and then the prostacyclin was added.

Although sodium hydroxide was used as base in the above example, any base may be used that is strong enough to give a buffer solution of the desired pH. Naturally the base should be one that gives rise to a pharmaceutically acceptable solution, i.e. one that is not deleterious to the recipient. The amount of amino-acid, for example, glycine and base, for example, sodium hydroxide, used should be as little as is necessary to stabilize the active compound for the period of time required. Use of excess of either or both amino-acid or base results in retention of water in a freeze dried product which brings about deterioration of the active compound. However, the pH of the solution is an important factor in assessing pharmaceutical acceptability. If the buffer solution is to be introduced into a machine for example in renal dialysis, then the pH can be up to 12 or even more, but if the buffer solution is to be administered in a large volume into a vein, for example in cardio-pulmonary by-pass, then the pH on entering the vein should preferably be in a range of from 8.4 to 9, and for this the pH of the buffer solution can be lowered shortly before use.

Other buffering agents may be present in the buffer solution but their amount should not substantially reduce the stability of the active compound in the solution. For example, some carbonate may be present, derived from the prostacyclin, e.g. prostacyclin sodium may contain up to 5% by weight of sodium carbonate.

As an active compound is very active pharmacologically, the amount of it needed is very small; for example only a few milligrams are needed for a one hour infusion into an average person of 70 kg body weight. The amount of active compound present in a given buffer solution before freeze drying depends on the projected use for the freeze dried material on reconstitution. The reconstitution may be with buffer solution free of active compound so that the ratio of active compound to buffering constituents may be much greater than in the solution used for administration.

If a solution containing only buffering agents, active compound and sodium chloride is freeze dried, the physical strength and appearance of the freeze dried plug obtained are not particularly satisfactory. It is accordingly preferred to include an excipient in the buffer solution before freeze drying the solution. The preferred excipient is mannitol. Preferably the concentration of excipient is from 25 to 50 mg/ml of buffer solution. For mannitol if less than 25 mg/ml is used there is insufficient improvement in strength and appearance. If more than 50 mg/ml is used there is little or no further improvement and the stability of the active compound may be adversely affected. The excipient provides, in the freeze dried plug, a supporting matrix and improves the physical strength and appearance of the plug. Not all excipients may be used; for example those producing excessive foaming of the reconstituted material in the freeze drying vial, e.g. polyvinylpyrrolidone, should be avoided. Also, others affecting the pH of the buffer, e.g. glycine itself, should be avoided.

The buffer solution may also contain, if desirable, other therapeutic material besides the active compound. A freeze dried product may also contain such other therapeutic material or these may be added to the reconstituted buffer solution. Such other therapeutic material may partly or completely replace the excipient.

The solvent used in preparing the buffer solution is preferably Water for Injections (European Pharmacopeia) or other water suitable for use in infusions or injections. When reconstituting the freeze dried material for use, it may be redissolved in Water for Injections generally having a pH value in the range of from 5.5 to 7, preferably 7, or in amino-acid buffer solution having a pH of at least 9, preferably about 10.5, or perhaps some of the buffer solution may be added to a solution in Water for Injections. Reconstitution of the freeze dried material may also take place by dissolving it in an infusion base, such as physiological saline suitable for infusion. It is also possible to use glucose for this purpose.

The freeze drying of the buffer solution may be carried out in any conventional manner, with the water content of the plug being lowered as far as convenient to improve further the stability of the active compound.

The amount of active compound required for therapeutic effect varies with the route of administration. In general, a suitable dose for a mammal will lie in the range of from 0.01 to 200 mg. per kilogram body weight, conveniently of from 0.01 to 10 mg/kg, preferably of from 0.1 to 1.0 mg/kg, and especially of from 0.2 to 0.5 mg/kg.

The amount of active compound present in an ampoule for administration by infusion will lie in the range of from 0.1 to 1.5 mg/kg, preferably of from 0.5–1.0 mg/kg. When used in man, the active compound may be several times more potent than in other mammals, and accordingly it may be desirable to use doses which appear at the lower ends of the dose ranges given hereinabove.

For human and veterinary use, it may be convenient to provide a collection of at least two vessels, for example as a multicomponent pack; one of which is a vial or ampoule containing a freeze dried (lyophilised) plug of the buffered active compound as described hereinabove, another vessel of which is a vial or ampoule containing a further amount of the buffer in aqueous solution or freeze dried which does not contain the active compound. The freeze dried product may then be reconstituted with the aqueous buffer, or where the contents of the second vessel are freeze dried, with a suitable aqueous diluent from a third vessel. The reconstituted material may then be diluted further, if required, to provide the desired dosage immediately prior to administration. Thus a freeze dried preparation of, for example 0.5 mg active compound, at pH 11.5 may be diluted, with 50 or 500 ml of aqueous dextrose or saline solution having a pH such that the resultant solution has a pH of 10.0 to 10.5.

Accordingly the present invention provides at least the following:

(a) A pharmaceutically acceptable buffer solution which comprises prostacyclin, 15-methylprostacyclin, 16,16-dimethylprostacyclin or a salt of any one of these, and, as principal buffering acid, an amino-acid, the solution having a pH of at least 9;

(b) A method of preparing a buffer solution according to (a), which comprises bringing the ingredients into solution in a suitable solvent;

(c) A freeze dried material obtained by freeze drying a buffer solution according to (a);

(d) A frozen injection obtained by freezing a buffer solution according to (a);

(c) A solution suitable for injection or infusion obtained by dissolving a freeze dried material according to (c) in a suitable solvent, or thawing a frozen injection according to (d);

(f) A method for administering prostacyclin, 15-methylprostacyclin 16,16-dimethylprostacyclin, or a salt of any one of these which comprises administering a solution according to (a), (d) or (c).

(g) A pharmaceutical formulation comprising an active compound selected from prostacyclin, 15-methylprostacyclin, 16,16-dimethylprostacyclin and a salt of any one of these in association with a pharmaceutically acceptable buffer having a pH of at least 9 and based on an amino acid as principal buffering acid in the buffer.

(h) A pharmaceutical formulation comprising an active compound selected from prostacyclin, 15-methylprostacyclin, 16,16-dimethylprostacyclin and a salt of any one of these in association with a pharmaceutically acceptable buffer based on an amino acid as the principal buffering agent.

The present invention is illustrated by the following Examples:

EXAMPLE 1

Sterile solutions containing prostacyclin (0.2 and 0.4 mg/ml) and mannitol (50 mg/ml) were prepared in the following buffers: glycine, orginine, valine, alanine, carbonate, and tris. The concentrations of the buffering components were:

Amino acid buffer: 0.025 M amino acid, 0.025 M sodium chloride and sodium hydroxide q.s. pH 10.5.
Carbonate buffer: 448 mg/l sodium bicarbonate and 1614 mg/l sodium carbonate.
Tris buffer: 6054 mg/l of tris base and 2.5 ml of 0.1 N sodium hydroxide per liter.

5 ml portions of each of these solutions were then freeze dried in vials by freezing at −40° C. and under vacuum, carrying out first stage drying at 0° C. and second stage drying at 20° C. Sealing of the vials was conducted in a nitrogen atmosphere. The freeze dried products were then subjected to an accelerated storage test at the temperature shown in Table I. The products obtained after the times indicated in Table I were analysed for their prostacyclin content by high performance liquid chromatography (HPLC). The HPLC was carried out on freeze dried preparations reconstituted in 10 ml of 0.025% tetramethylammonium hydroxide solution.

The column used was a 25 cm × 4.2 mm I.D. stainless steel one filled with laboratory prepared Partisil ODS packing material made as given below. The column was packed using the method of Webber and McKerrel, J. Chromatog., 122, 243, (1976), employing carbon tetrachloride as the slurry medium.

The column packing material was prepared as follows; 10 μm Partisil (10 g) was dried at 80° C. in vacuo for two and half hours in a 250 ml round bottomed flask. Octadecyltrichlorosilane (10 ml) and dry toluene (100 ml) were added and the solution was refluxed for three hours with paddle stirring using a reflux condenser fitted with a calcium chloride guard tube. The mixture was allowed to cool and then filtered through a 0.5 μm millipore filter. The silica in the filter was washed with 250 ml methanol, slurrying the solid continuously, then with 250 ml hot acetone and dried at 80° C. in vacuo for about two hours. The product (11 g) was treated with trimethylchlorosilane (10 ml) as above, refluxing for 45 minutes to give the final product.

The mobile phase used was water (1200 ml) in which was dissolved 5 g boric acid and 7.6 g di-sodium tetraborate and then methanol (800 ml) was added. The column temperature used was ambient i.e about 25° to 30° C., and the mobile phase flow rate was 3.6 ml/min. and the pressure used was 20 MPa. Detection of the products was carried out using a Pye Unichem LC3 at 205 nanometers wavelength, 0.16 aufs (absorbance units full scale) for 0 to 100 μg/ml solutions.

The amount of prostacyclin present was determined by peak height measurement and comparison with a reference sample of known concentration.

The results obtained are set out in Table I.

TABLE I

| Buffer | HPLC assay (% prostacyclin remaining) | | | | |
|---|---|---|---|---|---|
| | 66 hours | | | | 6 days (144 hours) |
| | 70° C. | 60° C. | 50° C. | 37° C. | 26° C. |
| Glycine | 0 | 0 | 3 | 90 | 96 |
| Arginine | | | | | |
| Valine | | | | | |
| Alanine | | | | | |
| Carbonate | 0 | 2 | 3.5 | 45 | 62 |
| Tris | 0 | 0 | trace | trace | 35 |

It can be clearly seen from Table I that at normal storage temperatures, i.e. about 37° C. or below, the amino-acid buffers, especially glycine, are superior to the other two buffers tested. Although the carbonate buffer is inferior to the amino-acid buffer it is clear that some carbonate could be tolerated in the amino-acid buffer.

EXAMPLE 2

| Freeze dried Injection of prostacyclin (1mg) | |
|---|---|
| Prostacyclin | 1.000 mg |
| Mannitol | 50.000 mg |
| NaCl (0.025M) | 2.932 mg |
| Glycine (0.025M) | 3.760 mg |
| NaOH | q.s. to pH 10.5 |

Using the general procedure give in Example 1, a 1 mg prostacyclin injection comprising the above ingredients was freeze dried to give a residue which may contain up to 5% w/w of water.

EXAMPLE 3

A stirred solution of $PGF_{2\alpha}$ methyl ester (50 mg) in ether (1 ml) was treated with sodium bicarbonate (115.0 mg; 10 molecular equivalents) and water (1 ml) and then dropwise during 2 hours with aqueous potassium triiodide (0.7 molar; 0.261 ml). After stirring overnight, the reaction mixture was shaken with ether and aqueous sodium thiosulphate; the etheral phase was separated, washed with water, dried with magnesium sulphate, and evaporated to leave a yellow gum of 5ξ-iodo-9-deoxy-6ξ,9α-epoxyprostaglandin $F_{1\alpha}$ methyl ester.

A solution of 5ξ-iodo-9-deoxy-6ξ,9α-epoxyprostaglandin $F_{1\alpha}$ methyl ester (100 mg) in methanolic sodium methoxide prepared from sodium (46 mg) and dry methanol (0.70 ml) was set aside under dry nitrogen for 5 hours, then freed from solvent in high vacuum. The residual amorphous solid was washed with benzene, set aside in the air overnight, and stirred with N aqueous sodium hydroxide (0.5 ml) to give a suspension of colourless fine needles. The crystals were collected, washed with a few drops of N aqueous sodium hydroxide, and dried in the air to give the sodium salt of 9-deoxy-6,9α-epoxy-$\Delta^5$-prostaglandin $F_{1\alpha}$. The inhibition of arachidonic acid-induced aggregation of human platelets at a concentration of 0.2 ng/ml by this salt and its instability in water at acid pH, together with further evidence, is compatible with assignation of the configuration (5Z)-5,6-didehydro-9-deoxy-6,9α-epoxyprostaglandin $F_{1\alpha}$.

The high-resolution $^{13}C$ n.m.r. spectrum of a solution of the crystals in dimethyl sulphoxide-$d_6$ showed the expected 20 resonances whose chemical shifts were entirely consistent with the chemical structure established for Prostacyclin. No impurity peaks were detected.

EXAMPLE 4

5ξ-Iodo-9-deoxy-6ξ,9ξ-epoxyprostaglandin $F_{1\alpha}$-methyl ester (500 ml) was stirred with methanolic NaOMe prepared from Na (0.23 g, 10 equivs.) and MeOH (3.5 ml) under $N_2$ at room temperature overnight; 1 N aq. NaOH (2.5 ml) was added to the yellow reaction solution to bring about hydrolysis of the ester moiety and, after 2 hours, the methanol was evaporated in vacuo at room temperature. The residual aqueous solution gave rise spontaneously to a mass of colourless fine needles of the desired sodium salt which was cooled (0°), collected, washed sparingly with 1 N aq. NaOH, air-dried, and stored in a stoppered tube; this salt (383 mg) had ν max (KBr disc) 1692 cm$^{-1}$.

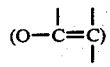

and twenty $^{13}C$ resonances only were observed at 182.7 (C-1), 158.2 (C-6), 140.0 and 134.3 (C-13,14), 100.7(C-5), 87.5(C-15), 80.6 and 75.5(C-9,11), 58.0(C-12), 49.0, 45.8, 42.4, 41.9, 37.5, 35.8(C-18), 31.6, 29.9, 29.3, 26.7(C-19), 18.4(C-20) ppm from TMS in DMSO-$d_6$). The product was sodium (5Z)-5,6-didehydro-9-deoxy-6,9α-epoxyprostaglandin $F_{1\alpha}$ (syn. sodium prostacyclin).

EXAMPLE 5

5ξ-Iodo-9-deoxy-6ξ,9α-epoxyprostaglandin $F_{1\alpha}$ methyl ester was treated with 1,5-diazabicyclo-5-nonene (DBN) at room temperature in the absence of a solvent for a few hours.

The DBN and hydrogen iodide were conveniently removed by adsorption on to a column of $SiO_2$, prepared from a suspension of $SiO_2$ in $EtOAc/Et_3N$ 50:1, and the vinyl ether was eluted with the same solvent system. I.R. spectroscopy (thin film, ν max 1738 ($CO_2Me$) and 1696 cm$^{-1}$

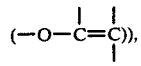

$^1H$ n.m.r. in $C_6D_6$—$Et_3N$, 19:1 (δ4.22, triplet of triplets$^{12}$, J6.9 and 1.0 Hz (C-5 vinyl proton)), and $^{13}C$ n.m.r. in $C_6D_6$—$Et_3N$, 19:1 (distinctive features were resonances at 159.8 (C-1), 155.8 (C-1), 155.8(C-6), 137.2 and 130.6(C-13,14), 95.3(C-5), 84.1(C-15) 77.3 and 72.2 (C-9,11) and 51.1 (Me ester) ppm from TMS).

The vinyl ether (5Z)-5,6-didehydro-9-deoxy-6,9α-epoxyprostaglandin methyl ester, was hydrolysed with aqueous sodium hydroxide to give synthetic sodium prostacyclin.

EXAMPLE 6

(5R, 6R)-5-Iodo-PGI$_1$ methyl ester (13.375 g, containing ca.2% 5S, 6S isomer) was taken up in methanolic sodium methoxide [from Na (6.23 g) and MeOH (94 ml)] at room temperature under $N_2$ and set aside at room temperature overnight. The resulting yellow solution was treated with 1 N aqueous NaOH (70 ml), filtered from sediment, set aside at room temperature for 2 hours, and freed from MeOH on a Buchi evaporator in vacuo at room temperature. The residual syrup was treated with $H_2O$ (25 ml) and with more 1 N aqueous NaOH (80 ml), crystallisation taking place spontaneously to give a mass of felted crystals. After cooling to 0°, the solid was collected, washed with ice cold 1 N aqueous NaOH (ca. 40 ml) until the washings were colourless, and dried in the air (2 days) to constant weight, affording 10.15 g, m.p. 164°-166° (following drying at 100°) of colourless prostacyclin sodium salt.

EXAMPLE 7

| Sterile Diluent for Injection of Prostacyclin | |
|---|---|
| Glycine (0.025M) | 94.0mg |
| NaCl (0.025M) | 73.3mg |
| NaOH | q.s. to pH 10.5 |
| Water for Injections up to | 50ml. |

Using the general procedure described in Example 1, the above ingredients were used in a solution for use as a diluent.

We claim:

1. A pharmaceutical formulation comprising an active compound selected from prostacyclin, 15-methylprostacyclin, 16, 16-dimethylprostacyclin or a pharmaceutically acceptable salt of any one of these in association with a pharmaceutically acceptable buffer having a pH of at least 9 and based on a pharmaceutically acceptable amino acid as a buffering acid in the buffer and, optionally, a further pharmaceutically acceptable carrier.

2. A formulation according to claim 1, wherein the further pharmaceutically acceptable carrier is or includes a solvent which dissolves the active compound and the buffer, to form a solution.

3. A formulation according to claim 1, wherein the further pharmaceutically acceptable carrier is or includes water.

4. A formulation according to claim 1, wherein a solution containing the active compound and the buffer is suitable for injection or infusion.

5. A formulation according to claim 1, wherein a solution containing the active compound and the buffer is freeze dried or frozen.

6. A formulation according to claim 1, wherein the amino-acid is sulphur-free.

7. A formulation according to claim 1, wherein the amino-acid is selected from the group consisting of glycine, alanine, arginine and valine.

8. A formulation according to claim 1, wherein the total concentration of the amino-acid including its salts, is in the range of from 0.02 to 0.03 M.

9. A formulation according to claim 1, wherein the total concentration of the amino-acid, including its salts, is about 0.025 M.

10. A formulation according to claim 1, wherein the further pharmecutically acceptable carrier comprises sodium chloride.

11. A formulation according to claim 1, wherein the pH of the buffer is in the range of from 10.2 to 10.8.

12. A formulation according to claim 1, wherein the further pharmaceutically acceptable carrier comprises an excipient.

13. A formulation according to claim 1, wherein the further pharmaceutically acceptable carrier comprises mannitol.

14. A formulation according to claim 1, wherein the active compound is prostacyclin or a salt thereof.

15. A formulation according to claim 1, wherein the salt is a sodium salt.

16. A formulation according to claim 1, wherein the active compound is prostacyclin sodium salt.

17. A formulation according to claim 1, comprising prostacyclin sodium salt in association with glycine and optionally, a further pharmaceutically acceptable carrier.

18. A method of preparing a pharmaceutical formulation according to claim 1, which comprises bringing an active compound selected from prostacyclin, 15-methylprostacyclin, 16,16-dimethylprostacyclin, and a salt of any one of these into association with a pharmaceutically acceptable buffer having a pH of at least 9 and based on an amino-acid as principal buffering acid in the buffer and, optionally, a further pharmaceutically acceptable carrier.

19. A formulation according to claim 1, when prepared by a method according to claim 18.

20. A method of inhibiting the aggregation of platelets, which comprises the bringing of said platelets into association with an amount of a formulation according to claim 1 containing an effective platelet aggregation inhibitory amount of the active compound.

21. A method of inducing vasodilation in a mammal, which comprises the administration to said mammal of an amount of a formulation according to claim 1 containing a non-toxic, effective vasodilatory amount of the active compound.

22. A method for the treatment or prophylaxis of thrombosis in a mammal or mammalian tissue which comprises administration of an amount of a formulation according to claim 1 containing a non-toxic, effective antithrombotic amount of the active compound.

23. A method of lowering blood pressure in a mammal which comprises administration to said mammal of an amount of a formulation according to claim 1 containing a non-toxic, effective hypotensive amount of the active compound.

24. A method for the treatment or prophylaxis of a gastric lesion in a mammal which comprises administration to said mammal of an amount of a formulation according to claim 1 containing a non-toxic, effective therapeutic or prophylactic amount of the active compound.

25. A method of stabilizing an active compound selected from the group consisting of prostacyclin, 15-methylprostacyclin, 16,16-dimethylprostacyclin and a pharmaceutically acceptable salt of any one of these against hydrolysis of the enol ether moiety, which method comprises bringing said compound selected from the group consisting of prostacyclin, 15-methylprostacyclin, 16,16-dimethylprostacyclin, and a pharmaceutically acceptable salt thereof into association with a pharmaceutically acceptable buffer having a pH of at least 9 and based on an amino acid as a buffering acid in the buffer.

26. A pharmaceutical formulation comprising an active compound selected from prostacyclin, 15-methylprostacyclin, 16,16-dimethylprostacyclin and a salt of any one of these in association with a pharmaceutically acceptable buffer based on an amino acid as principal buffering agent and buffered to a pH of at least 9.

27. A formulation according to claim 26, wherein the formulation further includes a base.

28. A pharmaceutical composition comprising prostacyclin or a pharmaceutically acceptable salt thereof in association with a pharmaceutically acceptable buffer having a pH of at least 9 and based on an amino acid as the principal buffering acid in the buffer.

29. The composition of claim 28 in which the amino acid is arginine.

30. The composition of claim 28 in which the amino acid is valine.

31. The composition of claim 28 in which the amino acid is alanine.

32. The composition of claim 28 in a form for injection, said composition including water.

33. A pharmaceutical composition comprising the sodium salt of prostacyclin in association with a pharmaceutically acceptable buffer having a pH of at least 9 and based on glycine as the acid in the buffer.

34. The composition of claim 33 in a form for injection, said composition including water.

* * * * *